US006844313B1

(12) United States Patent
Andersen

(10) Patent No.: US 6,844,313 B1
(45) Date of Patent: Jan. 18, 2005

(54) COMPOSITION CONTAINING A MEIOSIS ACTIVATING SUBSTANCE

(75) Inventor: Tina Meinertz Andersen, Horsholm (DK)

(73) Assignee: Novo Nordisk A/S, Bagsvaerd (DK)

( * ) Notice: Subject to any disclaimer, the term of this patent is extended or adjusted under 35 U.S.C. 154(b) by 208 days.

(21) Appl. No.: 09/661,696

(22) Filed: Sep. 14, 2000

(30) Foreign Application Priority Data

Sep. 16, 1999 (DK) ........................................ 1999 01308

(51) Int. Cl.[7] .......................... A01N 37/18; C12N 5/00; C12M 1/00
(52) U.S. Cl. .............................. 514/2; 435/2; 435/404; 435/405; 435/407; 435/283.1; 435/810
(58) Field of Search ........................ 514/2; 435/2, 404, 435/405, 407, 283.1, 810

(56) References Cited

U.S. PATENT DOCUMENTS

| 4,175,074 A | 11/1979 | Deshmukh | 260/121 |
|---|---|---|---|
| 4,751,219 A | 6/1988 | Kempen | 514/26 |
| 5,716,777 A | * 2/1998 | Byskov et al. | 435/2 |

FOREIGN PATENT DOCUMENTS

| WO | WO 90/03429 | 4/1990 |
|---|---|---|
| WO | WO 94/01090 | 1/1994 |
| WO | WO 96/00235 | 1/1996 |
| WO | WO 96/27658 | 9/1996 |
| WO | WO 97/00884 | 1/1997 |
| WO | WO 98/24883 | * 6/1998 |
| WO | WO 98/28323 | 7/1998 |
| WO | WO 98/55498 | 12/1998 |
| WO | WO 99/13914 | 3/1999 |
| WO | WO 99/61010 | 12/1999 |
| WO | WO 00/52142 | * 9/2000 |
| WO | WO 01/19354 A3 | 3/2001 |

OTHER PUBLICATIONS

Wang et al., Journal of Parenteral Science & Technology, vol. 42, Supplement pp. 4–26, 1988.*
Byskov et al., J. Mol Med. vol. 76, pp. 818–823 (1998).
Buch et al., Arch. Pharm. Pharm. Med. Chem., vol. 329, pp. 399–402 (1996).
Willebrand et al., Acta pharmacol. et toxicol., vol. 56, pp. 228–232 (1985).
Fukudome et al., Biochimica et Biophysica Acta, vol. 922, pp. 155–161 (1987).
Kurono et al., Chem. Pharm. Bull., vol. 35, pp. 3045–3048 (1987).
Beng et al., Clinica Chimica Acta, vol. 52, pp. 257–269 (1974).
Olson et al., Journal of Parenteral Science & Technology, vol. 42, pp. 82–85 (1988).
Tanaka et al., J. Pharmacobio–Dyn, vol. 9, pp. 1015–1022 (1986).
Fiume et al., Pharm. Acta Helv., vol. 60, pp. 318–320 (1985).

* cited by examiner

Primary Examiner—Jon Weber
Assistant Examiner—Abdel A. Mohamed
(74) Attorney, Agent, or Firm—Reza Green, Esq.; Richard W. Bork, Esq.; Marc A. Began, Esq.

(57) ABSTRACT

A solid composition containing a meiosis activating substance can be prepared by adding a protein or a phospergylcid.

27 Claims, No Drawings

COMPOSITION CONTAINING A MEIOSIS ACTIVATING SUBSTANCE

CROSS-REFERENCE TO RELATED APPLICATIONS

This application claims the benefit of Danish application PA 1999 01308 filed Sep. 16, 1999.

FIELD OF THIS INVENTION

The present invention relates to a solid product which can be used in connection with in vitro fertilisation.

BACKGROUND OF THIS INVENTION

Several meiosis activation substances (hereinafter designated MAS) have been found. When MAS are kept in a medium containing oocytes, the oocytes becomes more prone to become fertilised. However, a major problem with the use of MAS is that, usually, they have a very low solubility.

SUMMARY OF THIS INVENTION

One object of this invention is to develop a composition containing MAS or a derivative thereof which can be dissolved in an aqueous medium.

Another object is to develop a composition containing MAS or a derivative thereof which can be dissolved in an aqueous medium without any physical influence such as heating, stirring, or ultrasound treatment.

DETAILED DESCRIPTION OF THIS INVENTION

The solubility of a preferred MAS, i.e., FF-MAS, in water is very low, i.e., approximately 20 picogram/ml (corresponding to $2\times10^{-5}$ µg/ml), and in ethanol the solubility is substantially higher, i.e., approximately 4 mg/ml. According to our preliminary investigations, the highest solubility of FF-MAS in a mixture of ethanol and water (1:2.5) is approximately 0.4 mg/ml.

Several other MAS have a similar low solubility in water.

Surprisingly, it has now been found that a solid composition containing MAS and an additive have a good solubility in water. The additives are components which, when added to MAS, provides a composition which can be used to prepare an aqueous solution containing MAS.

Examples of additives are water soluble proteins such as serum albumin, e.g. human serum albumin (hereinafter designated HSA), optionally In recombinant form, enzymes and phospherglycerider such as phosphatidylethanolamin, phosphatidylcholine, phosphatidylserine, phosphatidynositol.

Preferably, the compositions of this invention have a content of water below 10%, preferably below 5%, more preferred below 1% (weight/weight).

Preferably, the compositions of this invention have a content of organic solvent below 10%, preferably below 5%, more preferred below 1% (weight/weight).

Preferably, the compositions of this invention have a content of MAS below 1%, preferably below 0.1%, more preferred below 0.05% (weight/weight).

Preferably, the compositions of this invention have a content of additive higher than 99%, more preferred higher than 99.9%.

Preferred compositions of this invention are such which can be treated with an aqueous medium containing no or only low concentrations of organic solvent result in a solution containing MAS. Preferably, these aqueous media contain less than 1%, preferably less than 0.5%, more preferred less than 0.1% of organic solvent (weight/weight).

Earlier, several attempts to prepare compositions fulfilling this requirement have failed.

Herein, the term MAS designates compounds which mediate the meiosis of oocytes. More specifically, MASs are compounds which in the test described in Example 1 below has a percentage germinal vesicle breakdown (hereinafter designated GVB) which is significantly higher than the control. Preferred MAS are such having a percentage GVB of at least 50%, preferably at least 80%. Examples of preferred MASs are 4,4-dimethyl-5 α-cholesta-8,14,24-triene-3β-ol (hereinafter designated FF-MAS); 4,4-dimethyl-5α-cholest-8,14,24-trien-3β-ol hemisuccinate; 5α-cholest-8,14-dien-3β-ol; 5α-cholest-8,14-dien-3β-ol hemisuccinate; (20S)-cholest-5-en-3β,20-diol; 3,hydroxy-4,4-dimethyl-5α-chola-8,14-dien-24-oic acid-N-(methionine) amide; and cholest-5-en-16β-ol. Further examples of MASs are mentioned in WO 96/00235, 96/27658, 97100884, 98/28323, 98/54965 and 98155498, more specifically in claim 1 thereof.

One way of preparing the compositions of this invention is to mix a solution of MAS in an organic solvent such as ethanol with an aqueous solution of the additive and, thereafter to wait until the solvent is evaporated. The evaporation can be accelerated by using continuous airflow over the product, vacuum, or any other feasible methods to remove the solvent. The product marketed could be a delivery system having one or more depressions or hollows. Hereinafter, these depressions and hollows are mutually designated hollows. At least one of these hollows contain a composition according to this invention. A convenient way of placing the solid MAS therein is first to place a solution containing MAS and the additive in the hollow and thereafter to evaporate the solution. In this way, the evaporation residue, i.e., the composition according to this invention, is placed directly in the hollow in said device (delivery system).

Since the composition of this invention is to be used for the treatment of oocytes, it is important that the composition of this invention does not contain constituents which influence the oocytes negatively.

One way of using the compositions of this invention is to dissolve the composition in an aqueous medium such as water and then, if desired, to add other constituents which may have a favourable influence on the maturation of the oocytes.

Another way of using the composition is to dissolved it in a media normally used for in vitro maturation.

The present invention is further illustrated by the following examples which, however, are not to be construed as limiting the scope of protection. The features disclosed in the foregoing description and in the following examples may, in any combination thereof, be material for realising the invention in diverse forms thereof.

Example 1

Method used for determining whether a compound is a MAS or not.

Oocytes were obtained from immature female mice (C57BL6J×DBA/2J F1, Bomholtgaard, Denmark) weighing 13–16 grams, that were kept under controlled temperature (20–22 ° C.), light (lights on 06.00–18.00) and relative humidity (50–70%). The mice received an intraperitoneal injection of 0.2 ml gonadotropins (Gonal-F, Serono) containing 20 IU FSH and 48 hours later the animals were killed by cervical dislocation. The ovaries were dissected out and the oocytes were isolated in Hx-medium (see below) under a stereo microscope by manual rupture of the follicles using a pair of 27 gauge needles. Spherical oocytes displaying an intact germinal vesicle (hereinafter designated GV) were divided in cumulus enclosed oocytes (hereinafter designated CEO) and naked oocytes (hereinafter designated NO) and placed in α-minimum essential medium (α-MEM without ribonucleosides, Gibco BRL, Cat. No. 22561) supplemented with 3 mg/ml bovine serum albumin (BSA, Sigma Cat. No. A-7030), 5 mg/ml human serum albumin. (HSA, State Serum Institute, Denmark), 0.23 mM pyruvate (Sigma, Cat. No S-8636), 2 mM glutamine (Flow Cat. No. 16–801), 100 IU/ml penicillin and 100 µg/ml streptomycin (Flow, Cat No. 16–700). This medium was supplemented with 3 mM hypoxanthine (Sigma Cat. No. H-9377) and designated Hx-medium.

The oocytes were rinsed three times in Hx-medium and oocytes of uniform size were divided into groups of CEO and NO. CEO and NO were cultured in 4-well multidishes (Nunclon, Denmark) in which each well contained 0.4 ml of Hx-medium and the compound to be tested in a concentration of 10 µM. One control well (i.e., 35–45 oocytes cultured in identical medium with no addition of test compound) was always cultured simultaneously with 3 test wells (3545 oocytes per well supplemented with test compound).

The oocytes were cultured in a humidified atmosphere of 5% $CO_2$ in air for 24 hours at 37° C. By the end of the culture period, the number of oocytes with GV, GVB and polar bodies (hereinafter designated PB), respectively, were counted using a stereo microscope (Wildt, Leica MZ 12). The percentage of GVB, defined as percentage of oocytes undergoing GVB per total number of oocytes in that well, was calculated as:

% GVB=((number of GVB+number of PB)/total number of oocytes)×100.

Example 2

Method used for determining whether a compound can be used as the additive in the compositions of this invention or not.

An additive for FF-MAS compositions are characterised by:
Improving the solubility of FF-MAS in ethanol/water (1:2.5 v/v)
Ensuring a clear solution of FF-MAS after reconstitution of the composition in MEM Alpha Medium.
Securing percent GVB is at least 50% preferable 80% when tested on oocytes obtained from immature female mice.

Prepare a saturated ethanolic solution of FF-MAS. Blend with an aqueous solution of the additive in the ration 1:2,5. By visual inspection control that surplus FF-MAS is available in the solution. Rotate the solution for 24 hours at room temperature. Filter the solution through 0,22 αm filter, determine the content of FF-MAS by HPLC and calculate the solubility. Transfer 350µl to 4-well dish and evaporate to dryness at room temperature. Add 500µl MEM AL- PHA medium (Gibcobal). If a clear solution is obtained within half an hour, the composition is tested on oocytes obtained from immature female mice. % GVB obtained is at least 50%, preferable 80%, vide example 1.

Example 3

Composition containing Human Serum Albumin (HSA).

In this example, 3 products were prepared. Referring to the table below, the stock solution of FF-MAS used for product 1, 2, and 3 contained 50, 500 and 3330 µg/ml, respectively. For each of the products, the stock solution of HSA contained 20% HSA. The amount of said stock solutions used is stated in the table. For example, for product 1, 400 µl of the FF-MAS stock solution was mixed with 1000 µl of the HSA stock solution. After mixing of these stock solutions, the solutions were clear, and no precipitation was observed therein. After mixing, the amount thereof stated in the table was transferred to 4-well multi-dishes (Nuclon, Denmark). For example, for product 1, 350 µl of the mixture was transferred to the multi-dish Finally, the solutions were evaporated to dryness at room temperature. After evaporation, some of he products appears as an opalescent, clear film in the dishes, other are invisible to the human eye. The highest concentration of FF-MAS dissolved in this example is 0.95 mg/ml.

Before use, 500 µl MEM ALPHA Medium (Gibcobal) is added, and a clear solution of FF-MAS and HSA is obtained within half an hour at room temperature.

|  | 4-well-multi dish No. 1 | 4-well-multi dish No. 2 | 4-well-multi dish No. 3 |
| --- | --- | --- | --- |
| FF-MAS solution in ethanol, 50 µg/ml | 400 µl | — | — |
| FF-MAS solution in ethanol, 500 µg/ml | — | 400 µl | — |
| FF-MAS solution in ethanol, 3.33 mg/ml | — | — | 450 µl |
| HSA solution in water, 20% | 1000 µl | 1000 µl | 1125 µl |
| Amount transferred to multi-dish | 350 µl | 350 µl | 525 µl |
| Ratio between FF-MAS and HSA | 1:10,000 | 1:1,000 | 1:150 |
| Appearance of solutions before evaporation | clear, colourless solutions, without precipitation | | |

EXAMPLE 4

Compositions containing Human Serum Albumin (HSA).

Analogously as described In the previous example, solutions of FF-MAS in water/ethanol containing HSA were prepared in the concentrations stated below by sample mixing at room temperature. After preparation, the solutions were clear, and no precipitation was observed. The solutions were transferred to 4-well multi-dishes (Nuclon, Denmark). Finally, the solutions were evaporated to dryness at room temperature.

Before use, 500 µl MEM ALPHA Medium (Gibcobal) is added, and within half an hour at room temperature, a clear solution of FF-MAS and HSA is obtained.

The formulations were tested on oocytes obtained from immature female mice. % GVB for the respective formulation are stated in the table below.

|  | 4-well-multi dish No. 1 | 4-well-multi dish No. 2 | 4-well-multi dish No. 3 |
|---|---|---|---|
| FF-MAS solution in ethanol, 5.22 μg/ml | 100 μl | — | — |
| FF-MAS solution in ethanol, 26.1 μg/ml | — | 100 μl | — |
| FF-MAS solution in ethanol, 261 mg/ml | — | — | 100 μl |
| HSA solution in water, 20% | 250 μl | 250 μl | 250 μl |
| Ratio between FF-MAS and HSA | 1:10,000 | 1:2,000 | 1:200 |
| Theoretical quantity of FF-MAS per well | 0.5 μg | 2.5 μg | 25 μg |
| % GVB | 72 | 93 | 91 |

EXAMPLE 5

Compositions containing Human Serum Albumin (HSA).

Analogously as described in the previous example, solutions of FF-MAS in water/ethanol containing HSA were prepared in the concentrations stated below by sample mixing at room temperature. After preparation, the solutions were clear, and no precipitation was observed. The solutions were transferred to Swell multi-dishes (Nuclon, Denmark). Finally, the solutions were evaporated to dryness at room temperature.

Before use, 500 μl MEM ALPHA medium (Gibcobal) is added, and within half an hour at room temperature, a clear solution of FF-MAS and HSA is obtained.

The concentration of FF-MAS after reconstitution was determined by HPLC, and the results are stated below. The formulations were tested on oocytes obtained from immature female mice. % GVB for the respective formulations are stated below.

|  | No. 1 | No. 2 | No. 3 | No. 4 | No. 5 |
|---|---|---|---|---|---|
| FF-MAS solution in ethanol, 26.1 μg/ml | 100 μl | — | — | — | — |
| FF-MAS solution in ethanol 7.83 μg/ml | — | 100 μl | — | — | — |
| FF-MAS solution in ethanol, 5.22 mg/ml | — | — | 100 μl | — | — |
| FF-MAS solution in ethanol, 2.5 μg/ml | — | — | — | 100 μl | — |
| FF-MAS solution in ethanol, 0.5 μg/ml | — | — | — | — | 100 μl |
| HSA solution in water, 20% | 250 μl | 250 μl | 250 μl | 250 μl | 250 μl |
| Ratio between FF-MAS and HSA | 1:100,000 | 1:20,000 | 1:10,000 | 1:6667 | 1:2000 |
| Theoretical quantity of FF-MAS per well | 0.05 μg | 0.25 μg | 0.5 μg | 0.75 μg | 2.5 μg |
| Percentage GVB | 13 | 52 | 78 | 82 | 90 |

What is claimed is:

1. An aqueous solution of a solid composition comprising a meiosis activating substance (MAS) and an additive which is a protein or a phosphoglyceride, wherein the solid composition has a content of protein or phosphoglyceride higher than 99% (weight/weight).

2. The aqueous solution of claim 1, comprising an organic solvent content of less than 0.1% (weight/weight).

3. A device comprising a hollow containing the solution of claim 1.

4. The aqueous solution of claim 1, where in the content of 4 MAS is at least 0.001 μg/ml.

5. The aqueous solution of claim 4, wherein the content of MAS is not more than 0.1 g/ml.

6. An aqueous solution comprising a meiosis activating substance (MAS) and an additive which is a protein or a phosphoglyceride, wherein the ratio of MAS to said protein or phosphoglyceride in said aqueous solution is at least 1:150 (weight/weight).

7. The solution of claim 6, wherein said solution comprises an organic solvent content of less an 0.1%.

8. The solution of claim 6, wherein the content of MAS is at least 0.001 μg/ml.

9. The solution of claim 8, wherein the content of MAS is not more than 0.1 g/ml.

10. The solution of claim 6, wherein said additive is a protein.

11. The solution of claim 10, wherein the protein is human seam albumin.

12. The solution of claim 11, wherein the human serum albumin is recombinant human serum albumin.

13. A solid composition comprising 4,4-dimethyl-5α-cholesta-8,14,24-triene-3β-ol and an additive which is a protein or a phosphoglyceride.

14. The composition of claim 13, wherein said composition has a content of water of below 10% (weight/weight).

15. The composition of claim 13, wherein said composition has a content of water of below 5% (weight/weight).

16. The composition of claim 13, wherein said composition has a content of water of below 5% (weight/weight).

17. The composition of claim 13, wherein said composition has a content of organic solvent of below 1% (weight/weight)).

18. The composition of claim 13, wherein said composition his a content of organic solvent of below 5% (weight/weight).

19. The composition of claim 13, wherein said composition has a content of organic solvent of below 1% (weight/weight).

20. The composition of claim 13, wherein said composition has a content of 4,4-dimethyl-5α-cholesta-8,14,24-triene-3β-ol of below 50% (weight/weight).

21. The composition of claim 13, wherein said composition has a content of 4,4-dimethyl-5α-cholesta-8,14,24-triene-3β-ol of below 20% (weight/weight).

22. The composition of claim 13, wherein said composition has a content of 4,4-dimethyl-5α-cholesta-8,14,24-triene-3β-ol of below 10% (weight/weight).

23. A device comprising a hollow containing the composition of claim 13.

24. The composition of claim 13, wherein said additive is a protein.

25. The composition of claim 24, wherein said protein is human serum albumin.

26. An aqueous solution comprising the composition of claim 13.

27. A device comprising a hollow containing the solution of claim 26.

* * * * *

UNITED STATES PATENT AND TRADEMARK OFFICE
CERTIFICATE OF CORRECTION

PATENT NO. : 6,844,313 B1
APPLICATION NO. : 09/661696
DATED : January 18, 2005
INVENTOR(S) : Tina Meinertz Andersen It is certified that error appears in the above-identified patent and that said Letters Patent is hereby corrected as shown below:

Column 6, line 25, Claim 11 – Change "seam" to --serum--

Column 6, line 36, Claim 16 – Change "below 5%" to --below 1%--

Column 6, line 38, Claim 17 – Change "below 1%" to --below 10%--

Signed and Sealed this

Thirty-first Day of July, 2007

JON W. DUDAS
*Director of the United States Patent and Trademark Office*